United States Patent [19]

Shapiro

[11] Patent Number: 5,024,236
[45] Date of Patent: Jun. 18, 1991

[54] PHOTOPROBE ASSEMBLY

[75] Inventor: Ronald S. Shapiro, Toledo, Ohio

[73] Assignee: Advanced Medical Technology, Inc., Monroe, Mich.

[21] Appl. No.: 253,488

[22] Filed: Oct. 5, 1988

[51] Int. Cl.⁵ ................................................ A61B 5/05
[52] U.S. Cl. ................................... 128/735; 128/395; 128/907
[58] Field of Search ......................... 128/735, 395, 907

[56] References Cited

U.S. PATENT DOCUMENTS

| | | | |
|---|---|---|---|
| 4,016,870 | 4/1977 | Lock | 128/735 |
| 4,535,784 | 8/1985 | Rohlicek et al. | 128/735 |
| 4,694,840 | 9/1987 | Kairis et al. | 128/735 |

FOREIGN PATENT DOCUMENTS

| | | | |
|---|---|---|---|
| 2431183 | 2/1975 | Fed. Rep. of Germany | 128/735 |
| 1126634 | 9/1968 | United Kingdom | 128/735 |

Primary Examiner—Kyle L. Howell
Assistant Examiner—John Hanley
Attorney, Agent, or Firm—Harness, Dickey & Pierce

[57] ABSTRACT

A relatively compact easily portable photoprobe assembly is disclosed which includes an electric probe for locating acupuncture points and a light emitting diode to stimulate acupuncture points as well as injury sites. The probe and light emitting diode are controlled by an internal circuit which operates to provide a visual indication of the precise location of the desired treatment area via an impedance variation procedure as well as to pulse the light emitting diode at the desired frequency. A power supply is also contained within the assembly to render it completely portable.

9 Claims, 3 Drawing Sheets

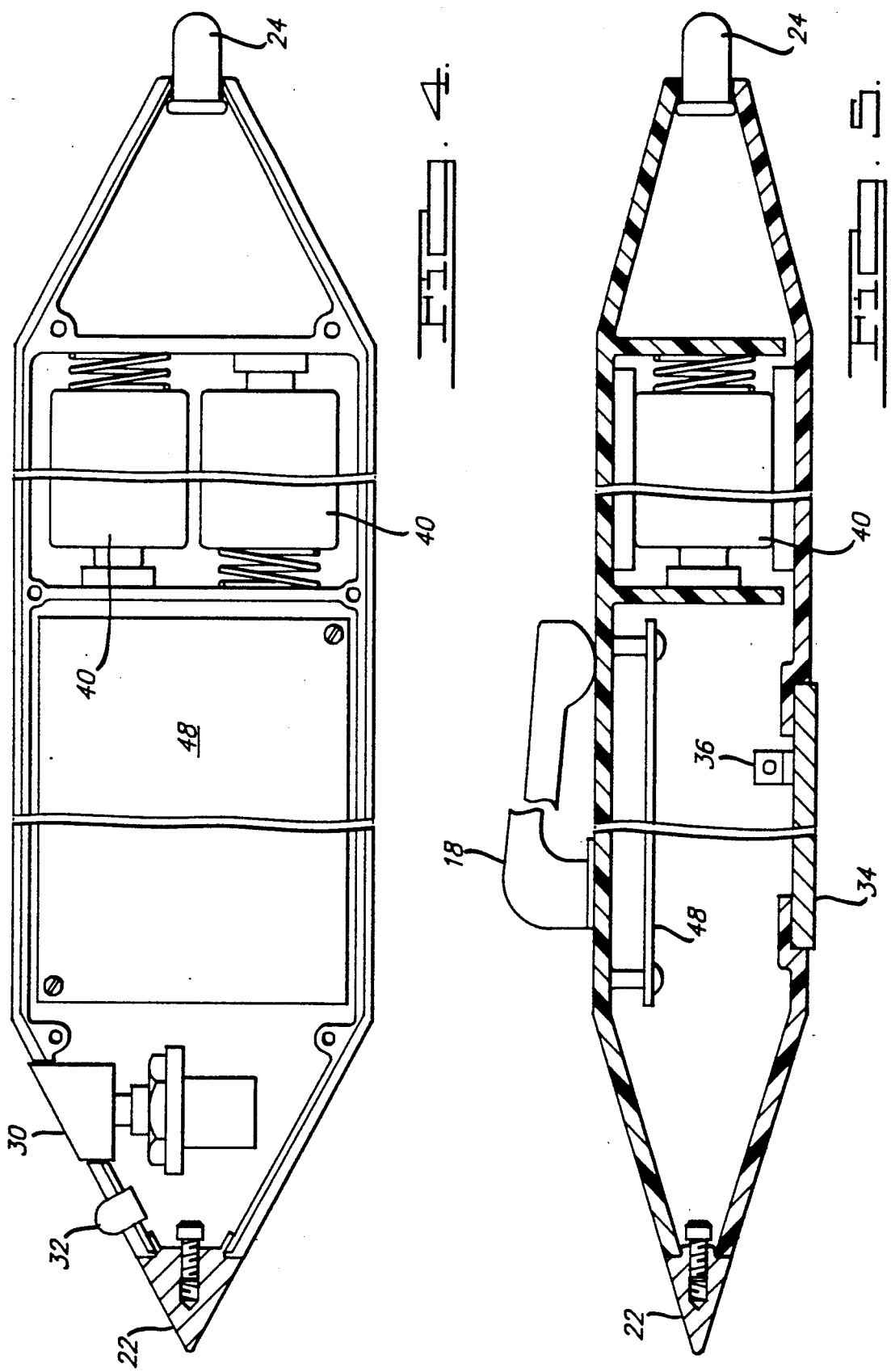

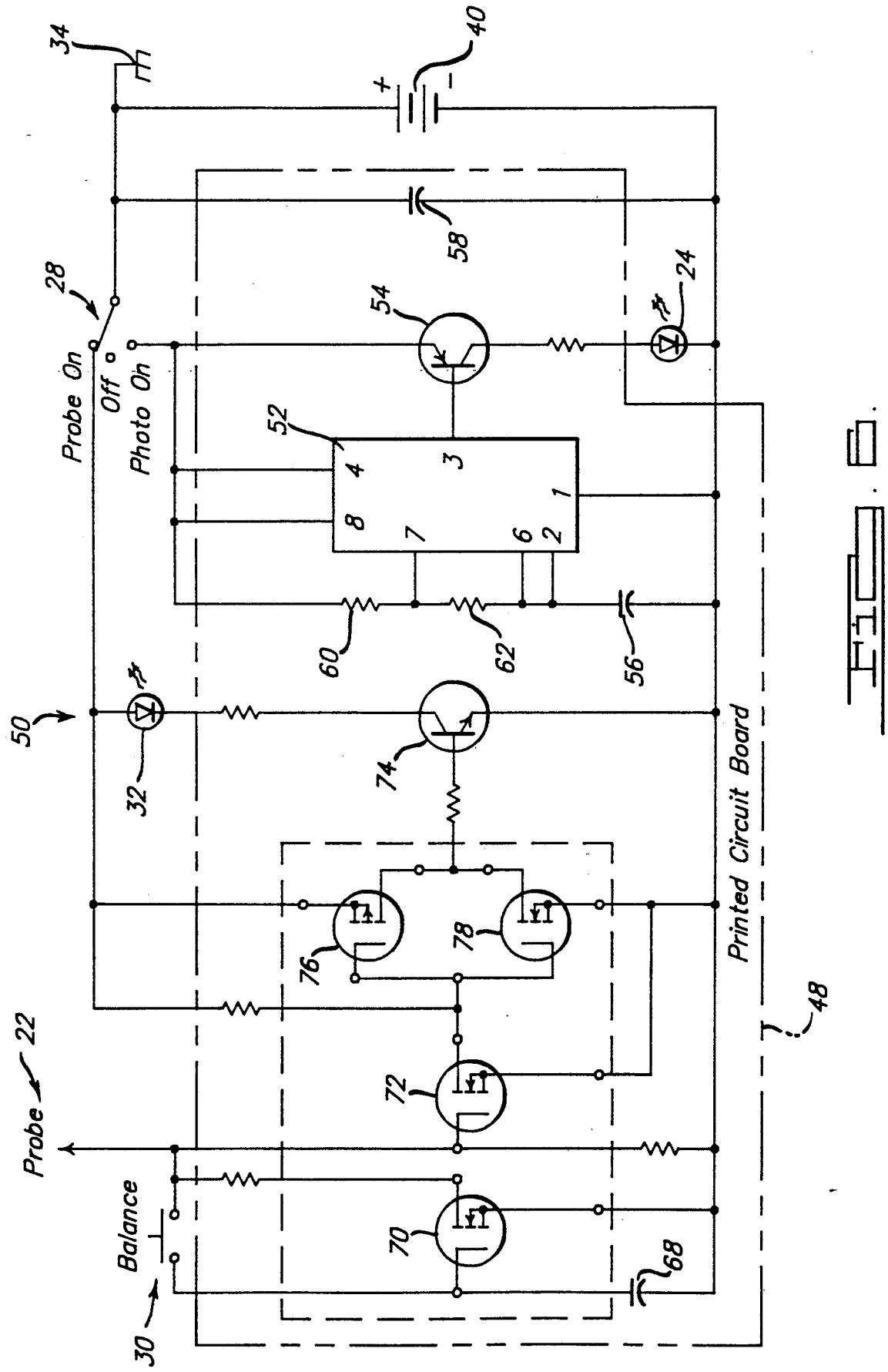

PHOTOPROBE ASSEMBLY

BACKGROUND AND SUMMARY OF THE INVENTION

This invention relates to an apparatus for first locating acupuncture points and then stimulating the points with light radiation for treatment purposes. Additionally, the apparatus can be used for applying light radiation directly to an injury to promote healing and relieve pain.

It is well known to stimulate acupuncture points by various means including applying needles, electric current, pressure, ultrasound, heat or light. It is also known that localization of acupuncture points can be accomplished by measuring the electrical impedance, which is considerably lower than the impedance of adjacent areas of skin.

A device is needed which can be used to both locate acupuncture points and to stimulate the points with light radiation. For convenient use, such a device should be portable and hand held.

Accordingly, it is an object of this invention to provide a portable device for first locating acupuncture points by detecting a decrease in the impedance of the subject's skin and also to provide a light source for stimulating the acupuncture point once located. Additionally, studies have indicated that light radiation directed toward an injury can have beneficial results in alleviating pain and promoting healing.

The apparatus of this invention includes an electric probe at one end for placement against the subject's skin to determine the impedance of the skin. Location of acupuncture points is determined by first determining a base line impedance of the subject's skin. This is accomplished by having the operator hold the photoprobe in one hand and touching the subject with the other hand. While touching a ground plate on the photoprobe case, the operator contacts the subject's skin with the electric probe of the photoprobe assembly. In so doing, a circuit is completed comprising the subject, the operator and the photoprobe assembly. The impedance of this circuit is determined using an integrated circuit within the photoprobe assembly. As the electric probe is moved on the subject's skin, the integrated circuit will indicate the location of decreased impedance, thereby indicating an acupuncture point.

A light emitting diode (LED) on the opposite end of the photoprobe can then be used to provide pulsed light radiation to stimulate the acupuncture point. The light pulse has a frequency of approximately 292 hertz and the light wave length is approximately 660 nanometers.

An integrated circuit is used to determine the location of decreased impedance and another integrated circuit is used to provide a desired frequency to the LED light radiation source. The apparatus is of a size which can be conveniently held in the hand of the operator and also stored in a shirt pocket when not in use. The device is powered by two 1½ volt AA batteries raking the device small, light weight, and convenient to use.

In addition to stimulating acupuncture points, the LED can also be used to directly stimulate various wounds and injuries to promote healing and alleviate pain. Examples of such injuries are contusions, scratches, and various open wounds. Treatment of these wounds can be accomplished by stimulating the wound with light radiation for a period of time ranging from one or two minutes to as many as ten minutes several times daily, or as needed, to relieve pain and promote healing. It should be noted that prior to receiving photo therapy, the subject should receive appropriate medical therapy for the condition. The photo therapy is used only for promotion of healing and alleviation of pain.

Further objects, features and advantages of the invention will become apparent from a consideration of the following description and the appended claims when taken in connection with the accompanying drawings.

BRIEF DESCRIPTION OF THE DRAWINGS

FIG. 4 is a bottom view similar to FIG. 2 showing the photoprobe with the cover plate removed;

FIG. 5 is a sectional view as seen from substantially the line 5—5 of FIG. 2; and FIG. 6 is a diagram of the integrated circuit used to locate acupuncture points and to provide pulsation of the LED used to stimulate the skin.

DETAILED DESCRIPTION OF THE DRAWINGS

Figure 1:
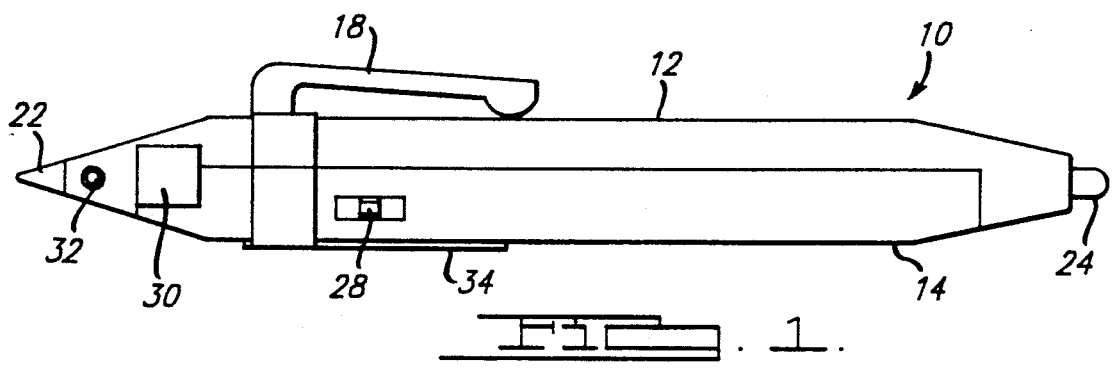
FIG. 1 is a side view of the photoprobe of this invention.
Figure 2:
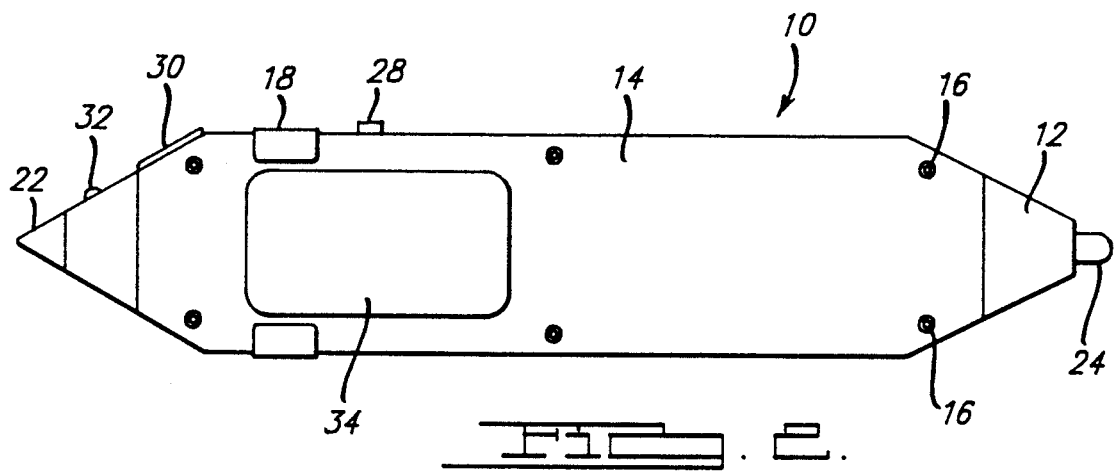
FIG. 2 is a bottom view of the probe of this invention.
Figure 3:
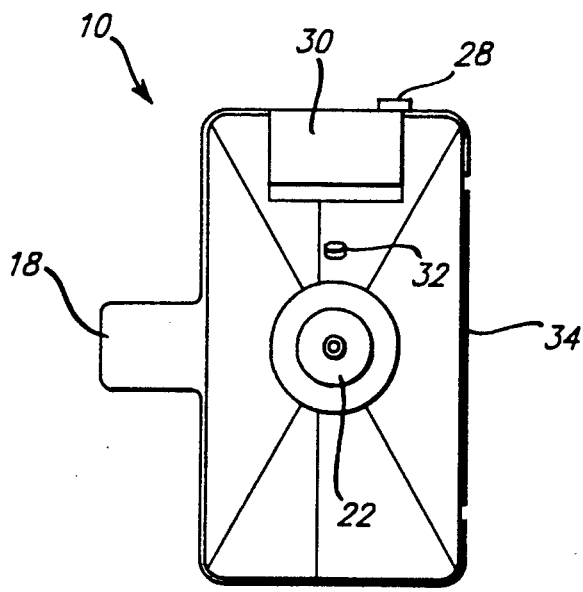
FIG. 3 is an end view of the probe of this invention.

Referring now to the drawings, the photoprobe of this invention is indicated generally at 10. The photoprobe includes a case 12 having a removable cover plate 14 retained by recessed allen screws 16. Preferably, case 12 will be fabricated from a suitable polymeric composition by injection molding for example. A pocket retainer clip 18 is used to hold the photoprobe in a shirt pocket. The photoprobe is preferably slightly less than seven inches in length, approximately 1⅜ inches wide and ¾ of an inch thick so as to render it suitable for easy storage in a shirt pocket and to comfortably fit in the hand during operation.

An electric probe 22 disposed at one end of the photoprobe 10 is used to locate acupuncture points by determining variations in the impedance of the subject's skin. The opposite end of the photoprobe 10 is equipped with a relatively high power light emitting diode (LED) 24. LED 24 is used to provide pulsed light radiation to the acupuncture points.

Switch 28 is a three position switch used to turn the device off in a first position, turn LED 24 on in a second position, and turn the probe 22 on in a third position. A momentary contact push button switch 30 is provided near the probe 22 end of the photoprobe. Disposed between contact switch 30 and the probe 22 is a second relatively low power LED 32. On the bottom of the photoprobe 10 is a stainless steel ground plate 34. The ground plate 34 is electrically connected through the electrical contact 36 with the contact switch 30, LED 32, probe 22, and batteries 40. These components are a part of the electric circuit 50 which controls the photoprobe functions. The remaining components of the circuit 50 are mounted on a printed circuit board 48.

In operation, to locate acupuncture points, the photoprobe switch 28 is first switched to the "probe on" position. The operator then grasps the photoprobe with his or her fingers contacting the ground plate 34 and with the thumb in position on contact switch 30. With the other hand, the operator touches the subject's skin. With the momentary contact switch 30 depressed, the operator contacts another portion of the subject's skin with the probe 22. When the photoprobe 10 contacts the skin of the subject, a circuit is completed between the photoprobe 10, the subject's body, the operator's body, the ground plate and circuit 50. In this manner, the photoprobe 10 determines a base line impedance in the completed circuit comprising both the subject and the operator. Once the base line impedance is determined, the operator can move the photoprobe to a general area where the desired acupuncture point is known to be located. Once the operator has touched the precise location of the desired acupuncture point with the probe 22, the photoprobe will detect a decrease in the skin impedance and the LED 32 will illuminate thereby providing a visual indication that the acupuncture point has thus been located.

Once the acupuncture point is located, the physician can press the probe lightly into the subject's skin leaving a small temporary dimple to indicate where the acupuncture point is. Having identified the acupuncture point, the operator then moves the photoprobe switch 28 to the "lamp on" position in which the LED 24 is energized. The operator then directs the LED 24 to the indicated acupuncture point to provide the desired light radiation stimulus to thus located acupuncture point.

The LED 24 provides non-coherent light at a spectral wave length of approximately 660 nanometers. The light intensity of LED 24 is approximately 5000 millicandles. The LED 24 is pulsed at a frequency of approximately 292 hertz and is thus suitable for stimulation of most areas of the body.

The frequency of LED 24 is controlled by a portion of the electrical circuit 50 shown in FIG. 6. An integrated circuit timer indicated at 52 is used to generate a square wave cycle which activates a transistor 54 to alternately energize and de-energize the LED 24 via the battery power source 40. Resistors 60 and 62 and tantalum dipped capacitor 56 are used to set the period of oscillation produced by the integrated circuit. Capacitor 56 is also used to provide frequency stability to integrated circuit 52 over a range of temperatures. Capacitor 58 is used to reduce spikes in the circuit energy draw required to illuminate the LED so as to increase the life expectancy of battery 40.

The remaining portion of circuit 50 is used to locate acupuncture points. This is accomplished by indicating points of lower impedance on the skin surface. With the operator holding the photoprobe 10 as described above with the probe 22 in contact with the subject's skin and with balance switch 30 closed, the probe measures the base line impedance of the circuit. The closure of balance switch 30 operates to enable capacitor 68 to be charged to some level thereby turning transistor 70 on which in turn will turn transistor 72 off. Once charged and with balance switch 30 released to an open condition, capacitor 68 will operate to maintain transistor 70 in an off condition which in turn retains transistor 72 in an on condition and transistor 74 in an off condition via the amplifier circuit which includes transistors 76 and 78 so long as the resistance across the probe, operator, subject and ground plate does not decrease below that initially encountered during establishment of the base line impedance or resistance. Thus, as the probe is lifted from the subject's skin into open air, the base level resistance will be maintained. Once the probe is moved into contact with an acupuncture point which as noted above offers a lower resistance, the otherwise stable bias on transistor 72 will be altered thus turning transistor 72 on. This in turn will result in transistor 74 being turned on via the action of transistors 76 and 78. Once transistor 74 becomes conductive, current will be allowed to flow through and illuminate LED 32 thereby providing a visual indication that an area of decreased resistance on the subject has been detected. The precise location of this point may then be marked in any suitable manner and the light radiation stimulus may then be applied to this point as described above.

It is to be understood that the invention is not limited to the exact construction or method illustrated and described above, but that various changes and modifications may be made without departing from the spirit and scope of the invention as defined in the following claims.

I claim:

1. An apparatus for detecting acupuncture points on the skin of a living subject by detecting an area of reduced skin impedance and for stimulating acupuncture points on the skin of a living subject by pulsed light radiation, comprising:

a housing;

a light emitting diode within said housing;

a probe provided on one end of said housing;

a source of electric current disposed within said housing;

first circuit means disposed within said housing for providing said light emitting diode with a pulsed current from said source of electric current; and second circuit means disposed within said housing and connected with said probe, said second circuit means including means for measuring an initial reference impedance for said living subject when said probe is placed in contact with said skin of said living subject at a first location and thereafter being operative to provide a signal indicative of an impedance less than said initial reference impedance of said subject when said probe is moved to another location on said skin of said living subject, said signal being indicative of an acupuncture point to be stimulated by said light emitting diode.

2. The apparatus of claim 1 wherein said light emitting diode has a wave length of approximately 660 nanometers.

3. The apparatus of claim 1 wherein said light emitting diode is pulsed at a frequency of approximately 292 hertz.

4. The apparatus of claim 1 wherein said housing is sized so as to be able to be hand held.

5. The apparatus of claim 1 wherein said electrical current source comprises a battery.

6. The apparatus of claim 1 wherein said second circuit means includes a second light emitting diode arranged to provide said signal.

7. The apparatus of claim 1 wherein said first circuit means includes an integrated circuit means to produce a square wave duty cycle to provide the pulsed current to said light emitting diode.

8. The apparatus of claim 1 wherein said second circuit includes a ground plate mounted on said housing, said probe and said ground plate being adapted to be engageable with spaced portions of the skin of said living subject whereby said reference impedance may be measured.

9. The apparatus of claim 8 wherein said second circuit means further includes a switch means, said switch means being operable to a first position whereby a first portion of said second circuit means is actuated for measuring said reference impedance and a second position whereby said first portion is deactuated and said impedance less than said reference may be sensed.

* * * * *